United States Patent [19]

Ishizaki et al.

[11] Patent Number: 5,223,632

[45] Date of Patent: Jun. 29, 1993

[54] 2,2'-BIS(DI-(3,5-DIALKYLPHENYL)PHOSPHINO)-1,1'-BINAPHTHYL AND TRANSITION METAL COMPLEX CONTAINING THE SAME AS LIGAND

[75] Inventors: Takerou Ishizaki; Yoji Hori; Hidenori Kumobayashi, all of Tokyo, Japan

[73] Assignee: Takasago International Corporation, Tokyo, Japan

[21] Appl. No.: 662,600

[22] Filed: Mar. 1, 1991

[30] Foreign Application Priority Data

Mar. 1, 1990 [JP] Japan ................... 2-50262

[51] Int. Cl.$^5$ .................................. C07F 15/00
[52] U.S. Cl. .................................. 556/21; 556/16
[58] Field of Search ................... 556/17, 18, 21, 16

[56] References Cited

U.S. PATENT DOCUMENTS 4,994,590 2/1991 Takaya et al. .............. 556/23 X
5,012,002 4/1991 Kumobayawshi et al. ......... 568/17

FOREIGN PATENT DOCUMENTS 0118257 2/1984 European Pat. Off. .
0135392 9/1984 European Pat. Off. .
0174057 3/1985 European Pat. Off. .

OTHER PUBLICATIONS

Communication Letter dated Jun. 12, 1991 and Search Report dated May 14, 1991.

*Primary Examiner*—Arthur C. Prescott
*Attorney, Agent, or Firm*—Sughrue, Mion, Zinn, Macpeak & Seas

[57] ABSTRACT

A 2,2'-bis[di-(3,5-dialkylphenyl)phosphino]-1,1'-binaphthyl represented by formula (I):

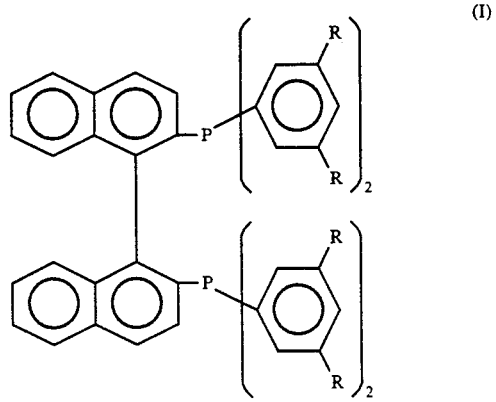

wherein R represents a lower alkyl group, is disclosed. A transition metal complex comprising a transition metal and a 2,2'-bis[di(3,5-dialkylphenyl)phosphino]-1,1'-binaphthyl represented by formula (I) as a ligand is also disclosed.

3 Claims, No Drawings

2,2'-BIS(DI-(3,5-DIALKYLPHENYL)PHOSPHINO)-1,1'-BINAPHTHYL AND TRANSITION METAL COMPLEX CONTAINING THE SAME AS LIGAND

FIELD OF THE INVENTION

The present invention relates to a novel phosphine compound and a transition metal complex containing the phosphine compound as a ligand. More particularly, it relates to a novel phosphine compound which forms complexes with metals such as ruthenium, rhodium, and palladium, thereby providing catalysts useful in various asymmetric synthesis reactions, and to such a metal complex.

BACKGROUND OF THE INVENTION

Hitherto, many reports have been made on transition metal complexes utilizable in organic synthesis reactions, for example, transition metal complex catalysts for use in asymmetric synthesis reactions such as asymmetric hydrogenation reaction, asymmetric isomerization reaction, and asymmetric silylation reaction. Among such transition metal complexes, most of the complexes in which optically active tertiary phosphine compounds are coordinated to transition metals such as ruthenium, rhodium, and palladium show excellent efficiency when used as catalysts in asymmetric synthesis reactions. For the purpose of further enhancing the efficiency of this kind of catalysts, a large number of phosphine compounds having special structures have been developed so far [see *Kagaku Sosetsu* (The Elements of Chemistry) 32, "Chemistry of Organometallic Complexes" pp. 237–238 (1982), edited by The Chemical Society of Japan]. 2,2'-Bis(diphenylphosphino)-1,1,-binaphthyl (hereinafter referred to as "BINAP") is one of the especially useful phosphine compounds, and a rhodium complex and a ruthenium complex each containing BINAP as a ligand have been reported in JP-A-55-61937 and JP-A-61-63690, respectively. (The term "JP-A" as used herein means an "unexamined published Japanese patent application".) It has also been reported that a rhodium complex (JP-A-60-199898) and a ruthenium complex (JP-A-61-63690) each containing 2,2'-bis[di-(p-tolyl) phosphino]-1,1'-binaphthyl (hereinafter referred to as "p-T-BINAP") as a ligand give good results when used in asymmetric hydrogenation reaction and asymmetric isomerization reaction.

However, there have been cases where according to the kind of the reaction to be conducted or to the reaction substrate therefor, sufficient selectivity, conversion, and durability cannot be obtained even when the above phosphine complexes are used.

In order to overcome the above-described problem, the present inventors have conducted intensive studies on many kinds of phosphine compounds. As a result, it has now been found that a BINAP derivative in which lower alkyl groups are introduced at the 3-position and 5-position in the phenyl groups thereof is far more effective in improving selectivity and conversion in asymmetric synthesis than BINAP and p-T-BINAP. The present invention has been completed based on this finding.

SUMMARY OF THE INVENTION

Accordingly, an object of the present invention is to provide a novel phosphine compound useful for producing transition metal complexes which, when used in various asymmetric synthesis reactions, bring about not only excellent selectivity and conversion of the substrates used in the reactions but also reaction durability, thus showing surprisingly improved catalytic efficiency as compared with conventional catalysts.

Another object of the present invention is to provide a transition metal complex containing said novel phosphine compound as a ligand.

In one aspect of the present invention, a novel phosphine compound is provided which is a 2,2'-bis[di (3,5-dialkylphenyl)phosphino]-1,1'-binaphthyl (hereinafter referred to as "3,5-DABINAP") represented by formula (I):

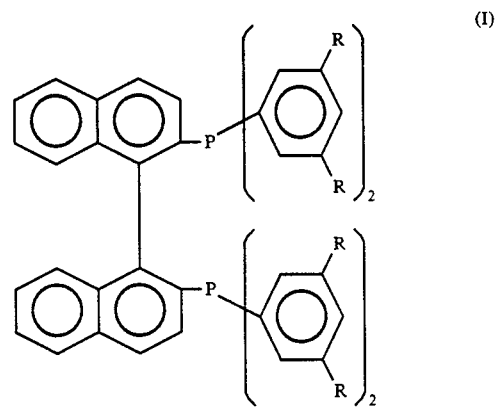

wherein R represents a lower alkyl group.

In another aspect of the present invention, a novel complex is provided which is a transition metal complex containing the 3,5-DABINAP as a ligand.

DETAILED DESCRIPTION OF THE INVENTION

The novel compound, 3,5-DABINAP, of the present invention is represented by formula (I) given above. In formula (I), R represents a lower alkyl group, preferably an alkyl group having from 1 to 4 carbon atoms. The 3,5-DABINAP of the present invention includes optically active isomers, the (+)-isomer and the (−)-isomer, and any of the (+)-isomer, the (−)-isomer, and racemate are included within the scope of this invention.

The 3,5-DABINAP of the present invention can, for example, be produced according to the following reaction schemes (1") and (2), in which R has the same meaning as that defined above.

Reaction Scheme (1):

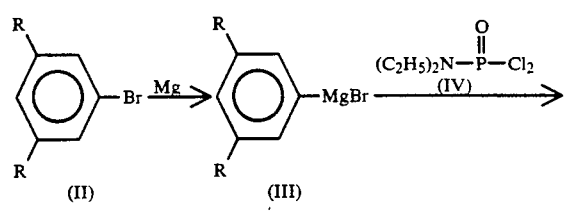

Reaction Scheme (1):

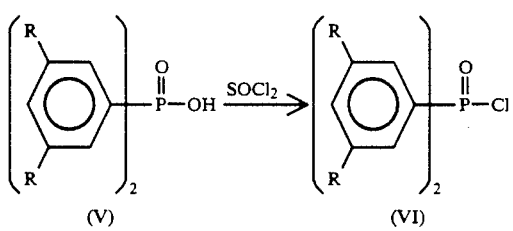

Reaction Scheme (2):

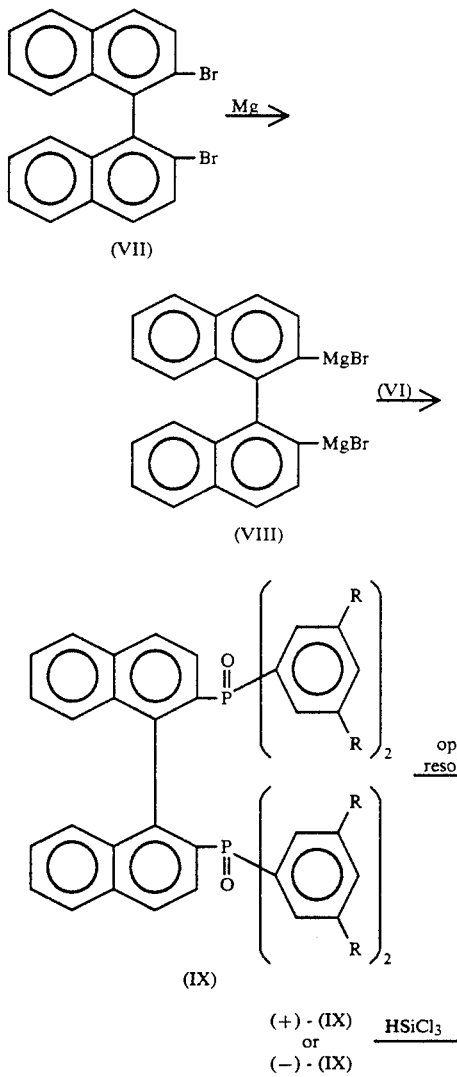

Illustratively stated, a 3-bromo-1,5-dialkylbenzene (II) is reacted with magnesium metal to prepare a Grignard reagent (III) which is then condensed with diethylamidophosphonic dichloride (IV) obtained by the method described in G.M. Kosolapoff et al., *J. Am. Chem. Soc.*, 71, pp. 369-370 (1949). The condensate is then hydrolyzed with hydrochloric acid to give a bis(3,5-dialkylphenyl)phosphinic acid (V). Thereafter, compound (V) is reacted with thionyl chloride, subsequently the excess thionyl chloride is removed, and the mixture is recrystallized from a benzene/hexane mixture to obtain a bis(3,5-dialkylphenyl)phosphonyl chloride (VI).

On the other hand, 2,2'-dibromo-1,1'-binaphthyl (VII) obtained by the method disclosed in JP-A-55-61937 is reacted with magnesium metal to give a Grignard reagent (VIII) which is then reacted with compound (VI) synthesized above, thereby synthesizing a 2,2'-bis[di-(3,5-dialkylphenyl)phosphoryl]-1,1'-binaphthyl (IX). This racemic compound (IX) is dissolved with heating in carbon tetrachloride, an ether solution of (−) dibenzoyltartaric acid is added thereto, and the resulting mixture is then stirred whereby crystals are deposited. The resulting crystals are recrystallized likewise. The same procedures are repeated until the optical rotation of the crystals comes to be constant. The thus-purified crystals are suspended in methylene chloride, and 2N sodium hydroxide is added thereto, thereby obtaining a free phosphine oxide (IX) as a (−)-isomer. By conducting the same optical resolution as the above except that (+)-dibenzoyltartaric acid is used, a free phosphine oxide (IX) as a (+)-isomer is obtained. Finally, by reducing the (−)-isomer or (+)-isomer of compound (IX) with trichlorosilane, the (−)-isomer or (+)-isomer of a 3,5-DABINAP according to the present invention can be obtained.

As a ligand, the 3,5-DABINAP of the present invention forms a complex with a transition metal. Examples of such a transition metal for forming the above complex include rhodium, palladium, and ruthenium.

The transition metal complex according to the present invention may, for example, be produced by the following methods. In one method, [Rh(CO)$_2$Cl]$_2$ is reacted with the 3,5-DABINAP of this invention to obtain Rh(CO)Cl(3,5-DABINAP). Alternatively, [RuCl$_2$(p-cymene)]$_2$ prepared by the method described in M. A. Bennett, *J. Chem. Soc. Dalton*, pp. 233-241 (1974) is treated with potassium iodide to give [RuI$_2$(p-cymene)]$_2$ which is then reacted with the 3,5-DABINAP of this invention to obtain [RuI(p-cymene)(3,5-DABINAP)]$^+$I$^-$.

The thus-obtained transition metal complex, when used as a catalyst in an asymmetric synthesis reaction, for example, in the asymmetric hydrogenation reaction of a β-keto ester, gives a reduction product with a high optical purity in a high optical yield. Furthermore, when either the (−)-isomer or (+)-isomer of the 3,5-DABINAP according to the present invention is selected to prepare a transition metal complex which contains the selected isomer as a ligand and this complex is used as a catalyst in an asymmetric synthesis reaction, an intended compound having the desired absolute configuration can be obtained.

As described above, the 3,5-DABINAP of the present invention can be an excellent ligand in catalysts for use in asymmetric synthesis. The complex of this 3,5-DABINAP with a transition metal such as ruthenium, rhodium, and palladium shows excellent catalytic activity when used as a catalyst in various asymmetric syntheses such as asymmetric hydrogenation, asymmetric isomerization, and asymmetric silylation. Therefore, by use of this transition metal complex, optically active compounds having high optical purities can be produced.

The present invention will be explained below in more detail by reference to the following examples, which should not be construed to be limiting the scope of the invention.

In the examples, the following analysis and measurements were conducted using apparatus specified below.

NMR: Model AM-400 (400 MH$_2$) (manufactured by Bruker Inc.) Internal reference: $^1$H-NMR . . . . tetramethylsilane; External reference: $^{31}$P-NMR . . . 85% phosphoric acid Optical Rotation: Model DIP-4 (manufactured by Nippon Bunko Kogyo K.K.)

Optical Purity: High-speed liquid chromatography . Waters Liquid Chromatography Model 510 (manufactured by Nippon Millipore Ltd.")

Detector: UV detector Lambda-Max Model 481 (manufactured by Nippon Millipore Ltd.)

EXAMPLE 1

Synthesis of bis(3,5-dimethylphenyl)phosphinic acid (V-1)

111 g (0.6 mole) of 3-bromo-1,5-dimethylbenzene was reacted with 14.6 g (0.6 mole) of magnesium metal in 350 ml of dehydrated THF (tetrahydrofuran), thereby preparing a Grignard reagent. 57 g (0.3 mole) of diethylamidophosphonic dichloride was added dropwise thereto under reflux over a period of 2 hours. The resulting mixture was heated under reflux for an additional 2 hours to allow it to react. Thereafter, 400 ml of ice water and 150 ml of a saturated aqueous solution of ammonium chloride were added to the reaction mixture to decompose the salt. The THF layer was separated from the aqueous layer, 500 ml of concentrated hydrochloric acid was added to the THF layer with ice-cooling, and the mixture was reacted at 80° C. for 5 hours. The resulting precipitate was filtered off, washed with water, and then dried, thereby obtaining 81.2 g of a crude product. This crude product was added to 1 liter of an aqueous solution of 17.8 g of sodium hydroxide to give a uniform solution. The insoluble matter was removed by filtration, and 20% sulfuric acid was added to the filtrate to neutralize it and then further make it acidic. The resulting precipitate was filtered off, washed with water, and then dried, thereby obtaining 62.7 g of purified bis-(3,5-dimethylphenyl)phosphinic acid as a colorless solid (yield 76%, m.p. 256°–261° C.).

EXAMPLE 2

Synthesis of bis(3,5-dimethylphenyl)phosphonyl chloride (VI-1)

63 g (0.23 mole) of the bis(3,5- dimethylphenyl)phosphinic acid as obtained in Example 1 was suspended in 120 ml of toluene. 35.6 g (0.299 mole) of thionyl chloride was added dropwise to the suspension at 50° to 55° C. over a period of 3 hours. After the resulting mixture was cooled to room temperature, the insoluble matter was removed by filtration. The toluene was then removed from the filtrate at atmospheric pressure, and the residue was poured into 300 ml of hexane. The crystals precipitated were quickly filtered off and dried, thereby obtaining 51.6 g of bis(3,5-dimethylphenyl)phosphonyl chloride as a colorless solid (yield 76.7%, m.p. 108°–109° C.).

EXAMPLE 3

Synthesis of 2,2'-bis[(di-3,5-dimethylphenyl) phosphoryl]-1,1'-binaphthyl (IX-1)

17.4 g (0.038 mole, purity 90%) of 2,2'-dibromo-1,1'-binaphthyl was reacted with 2.23 g (0.092 mole) of magnesium metal in a mixture of 270 ml of toluene and 30 ml of tetrahydrofuran, thereby preparing a Grignard reagent. 25 ml of a toluene solution of 23.4 g (0.08 mole) of the bis(3,5-dimethylphenyl)phosphonyl chloride as obtained in Example 2 was added thereto, and the mixture was reacted at 40° C. The tetrahydrofuran and toluene were then recovered at atmospheric pressure, and 200 ml of toluene and 200 ml of water were added to the residue. 10 ml of 10% sulfuric acid was added thereto, and the mixture was stirred at 60° C. for 30 minutes, followed by liquid separation and washing with warm water. Subsequently, 100 ml of water and 10 ml of a saturated aqueous solution of sodium carbonate were added, and the resulting mixture was stirred at 60° C. for 30 minutes and then washed once with warm water. After liquid separation, the solvent was removed by evaporation. The residue was dissolved in a small amount of toluene, and 500 ml of hexane was added to this solution. The resulting precipitate was filtered off and recrystallized from a mixture of 125 ml of toluene and 125 ml of hexane, thereby obtaining 19.9 g of 2,2'-bis[di-(3,5-dimethylphenyl)phosphoryl]-1,1'-binaphthyl as a colorless solid (yield 64.9%, m.p. 287°–290° C.).

EXAMPLE 4

Optical resolution of 2,2'-bis[di-(3,5-dimethylphenyl)phosphoryl]-1,1'-binaphthyl 5.6 g (7.30 mmole) of the 2,2'-bis[di-(3,5-dimethylphenyl)phosphoryl]-1,1,-binaphthyl which was a racemate as obtained in Example 3 was dissolved in 80 ml of carbon tetrachloride at 40° C. A solution of 2.62 g (7.31 mmole) of (−)-dibenzoyltartaric acid in 100 ml of diethyl ether was added thereto. After the resulting mixture was cooled to room temperature, hexane was added thereto to form a precipitate which was separated and dried to obtain a diastereomer mixture consisting of a same-sign salt [(−)(−)-salt] and a different-sign salt [(+)(−)-salt]. 0.8 g (0.71 mmole) of this salt was dissolved in 2.5 ml of carbon tetrachloride at 60° C., and the solution was then cooled to 40° C. To this solution was added slowly 25 ml of diethyl ether with stirring. The resulting solution was cooled to room temperature while stirring, whereby a precipitate was deposited. This mixture was stirred for an additional 1 hour, and the precipitate was filtered off, thereby obtaining 0.27 g of a sparingly soluble same-sign diastereomer [(−)(−)-salt]. The optical rotation of this diastereomer was measured, and the above procedures were repeated until the optical rotation value came to be constant. Subsequently, about 40 ml of each of 2-N sodium hydroxide and methylene chloride was added to the purified salt for neutralization, and the salt was completely dissolved with stirring. After liquid separation, the aqueous layer was subjected to extraction with about 20 ml of methylene chloride two or three times. The methylene chloride layer was dried by adding thereto a proper amount of potassium carbonate. The resulting mixture was filtered and the solvent was removed from the filtrate by evaporation under reduced pressure, thereby obtaining (−)-2,2'-bis[di-(3,5-dimethylphenyl)-phosphoryl]-1,1'-binaphthyl, (−)-(IX-1). The thus obtained optically active isomer, (−)-(IX-1), was recrystallized repeatedly from a 1:10 (by volume) mixed solvent of carbon tetrachloride and diethyl ether until the optical rotation of the crystals came to no longer fluctuate.

Further, the same procedures as the above were repeated except that (+)-dibenzoyltartaric acid was used, thereby obtaining (+)-2,2'-bis[di-(3,5-dimethylphenyl)-phosphoryl]-1,1'-binaphthyl, (+)-(IX-1).

[α]$_D^{25}$ for (+)-isomer: +220.5° (c=1, chloroform).
[α]$_D^{25}$ for (−)-isomer: −220.8° (c=1, chloroform).

The optical purity of the (+)-isomer or (−)-isomer was determined by high-speed liquid chromatography under the following conditions and found to be 99.5% ee.

Column: Chiralcel OD, φ0.46 cm×25 cm (manufactured by Daicel Chemical Industries, Ltd., Japan)
Developing solvent: hexane/isopropanol=9/1 (by volume; hereinafter all solvent ratios are given by volume)
Flow rate: 1 ml/min
Detection wavelength: UV-254 nm

EXAMPLE 5

Synthesis of (−)-2,2'-bis[di-(3,5-dimethylphenyl)phosphino]-1,1'-binaphthyl, (−)-(I-1)

To 0.77 g (1.00 mmole) of the optically active compound (−)-(IX-1) as obtained in Example 4 were added 6.5 ml of xylene and 2.7 ml (19.37 mmole) of triethylamine. After the optically active compound was dissolved by stirring, 1.7 ml (16.87 mmole) of trichlorosilane was added dropwise thereto over a period of 20 to 30 minutes. The mixture was reacted at 100° C. for 1 hour, at 120° C. for 1 hour, and then at 145° C. for 4 hours. The reaction mixture was then cooled to room temperature, and 8.5 ml of xylene and 10 ml of a 30% sodium hydroxide solution were added thereto. The resulting mixture was stirred at 70° C. for 30 minutes, followed by liquid separation. The organic layer was washed with water and dried over magnesium sulfate, and the toluene was then removed by evaporation under reduced pressure to obtain 0.62 g of a reduction prtoduct. This product was resolved by silica gel column chromatography (hexane:ethyl acetate=8:1), thereby obtaining 0.24 g (yield 32.7%) of (−)-2,2'-bis[di-(3,5-dimethylphenyl)-phosphino]-1,1'-binaphthyl (hereinafter referred to as "(−)-3,5-DMBINAP").

Further, the same procedures as the above were repeated except that the optically active compound, (+)-(IX-1), as obtained in Example 4 was used. Thus, 0.22 g (yield 30.0%) of (+)-2,2'-bis[di-(3,5-dimethylphenyl)phosphino]-1,1'-binaphthyl was obtained.

[α]$_D^{25}$ for (+)-isomer: +163.3° (c=1, chloroform).
[α]$_D^{25}$ for (−)-isomer: −163.7° (c=1, chloroform).

EXAMPLE 6

Synthesis of [RuI(p-cymene)((−)-3,5-DMBINAP)]$^+$I$^-$

In a mixed solvent of 50 ml of water and 50 ml of methylene chloride were dissolved 2.0 g (3.27 mmole) of [RuCl$_2$(p-cymene)]$_2$, 1.8 g (10.84 mmole) of potassium iodide, and 0.07 g (0.35 mmole) of tetramethylammonium iodide. This solution was stirred at room temperature for 4 hours, followed by liquid separation. The aqueous layer was removed, the residue was washed once with 50 ml of water, and the methylene chloride was then removed by evaporation under reduced pressure (20 mmHg). The residue was dried at room temperature under a high vacuum (0.2 mmHg), thereby obtaining 3.03 g (yield 95%) of a reddish brown complex, [RuI$_2$:(p-cymene)]$_2$.

$^1$H-NMR(CD$_2$Cl$_2$)δppm: 1.25 (d, 6H, J=6.93 Hz) 2.35 (s, 3H) 3.00 (hep, 1H, J=6.93 Hz) 5.42 (d, 2H, J=5.96 Hz) 5.52 (d, 2H, J=5.96 Hz).

In a mixed solvent of 5.4 ml of ethanol and 2.75 ml of methylene chloride were dissolved 0.0296 g (0.03 mmole) of the above-obtained complex and 0.0504 g (0.0671 mmole) of the (−)-3,5-DMBINAP as obtained in Example 5. The solution was reacted at 50° C. for 1 hour. The reaction mixture was concentrated to dryness, thereby quantitatively obtaining 0.08 g of the titled complex.

Elemental analysis for C$_{62}$H$_{62}$I$_2$P$_2$Ru: Calculated: C:60.84% H:5.11%. Found: C:60.97% H:5.25%.

$^{31}$P-NMR(CD$_2$Cl$_2$)δppm: 25.73 (d, J=57.8 Hz). 39.36 (d, J=58.5 Hz).

EXAMPLE 7

Synthesis of Rh(CO)Cl((−)-3,5-DMBINAP)

In 3.0 ml of methylene chloride were dissolved 0.0261 g (0.067 mmole) of [Rh(CO)$_2$:Cl]": and 0.1008 g (0.134 mmole) of the (−)-3,5-DMBINAP as obtained in Example 5. The solution was reacted at room temperature for 30 minutes. The reaction mixture was concentrated to dryness, thereby quantitatively obtaining 0.127 g of the titled complex.

Elemental analysis for C$_{53}$H$_{48}$ClOP$_2$Rh Calculated: C:70.63% H:5.37%. Found: C:70.94% H:5.53%. $^{31}$P-NMR(CD$_2$Cl$_2$)δppm: 23 10 (dd, J=126.6, 42.2 Hz); 47.05 (dd, J=161.7, 42.2 Hz).

EXAMPLE 8

Asymmetric hydrogenation reaction of methyl 2-benzamidomethyl-3-oxobutanoate

Into a 100-ml stainless-steel autoclave the inside of which had been replaced with nitrogen beforehand were introduced 5.01 g (20.1 mmole) of methyl 2-benzamidomethyl-3-oxobutanoate, 20 ml of methanol, and 28.3 mg (0.023 mmole) of [RuI(p-cymene)((−)-3,5-DMBINAP)]$^+$I$^-$. The hydrogenation reaction of the methyl ester was conducted for 20 hours under conditions of a hydrogen pressure of 50 kg/cm$^2$ and 50° C. After the reaction, the solvent was removed by evaporation to obtain 3.13 g of a hydrogenation product. This product was resolved by silica gel column chromatography (hexane/isopropanol =85:15), and then the structure of each of the separated components was examined by $^1$H-NMR spectroscopy. As a result, it was ascertained that two diastereomer components had formed.

$^1$H-NMR (CDCl$_3$)δppm:

Component A: 1.26 (d, 3H, J=6.25 Hz) 2.60–2.64 (m, 1H) 3.57–3.62 (m, 1H) 4.00–4.03 (m, 1H) 3.73 (s, 3H) 4.08–4.14 (m, 1H) 7.27 (br, s, 1H) 7.41–7.45 (m, 2H) 7.49–7.53 (m, 1H) 7.77–7.80 (m, 1H) Component B: 1.30 (d, 3H, J=6.28 Hz) 2.84–2.86 (m, 1H) 3.74 (s, 3H) 3.71–3.77 (m, 1H) 3.85–3.91 (m, 1H) 4.09–4.14 (m, 1H) 6.92 (br, s, 1H) 7.40–7.44 (m, 2H) 7.48–7.50 (m, 1H) 7.74–7.76 (m, 1H)

The conversion and the ratio of the formed two diastereomer components were determined by high-speed liquid chromatography under the following conditions. As a result, it was found that the conversion was 62.5% and the diastereomer ratio A/B was 86.5/13.5 by weight.

Column: Cosmocil, φ0.46 cm×25 cm (manufactured by Nakarai Tesuku Co.)
Eluant: hexane/chloroform/methanol =900/100/20
Flow rate: 2 ml/min Detection wavelength: UV-254 nm Further, each component isolated by silica gel column chromatography (hexane:ethyl acetate =1:1) was converted into methoxytrifluoromethyl phenylacetate and analyzed by high-speed liquid chromatography under the following conditions. As a result, the optical purity of Component A was found to be 96% ee.

Column: Cosmocil, $\phi$0.46 cm×25 cm (manufactured by Nakarai Tesuku Co.)
Eluant: hexane/tetrahydrofuran/methanol=100/100/1
Flow rate: 1 ml/min
Detection wavelength: UV-254 nm

COMPARATIVE EXAMPLE

Into a 100-ml autoclave the inside of which had been replaced with nitrogen beforehand were introduced 5.27 g (21.1 mmole) of methyl 2-benzamidomethyl-3-oxobutanoate, 21 ml of methanol, and 23.5 mg (0.022 mmole) of [RuI(p-cymene)((−)-BINAP)]$^+$I$^-$. The hydrogenation reaction of the methyl ester was conducted for 20 hours under conditions of a hydrogen pressure of 50 kg/cm$^2$ and 50° C.

In the same manner as in Example 8, the conversion, diastereomer ratio, and optical purity were determined. As a result, it was found that the conversion was 49.4%, the diastereomer ratio A/B was 80.8/19.2, and the optical purity of Component A was 95% ee.

While the invention has been described in detail and with reference to specific embodiments thereof, it will be apparent to one skilled in the art that various changes and modifications can be made therein without departing from the spirit and scope thereof.

What is claimed is:

1. A transition metal catalyst comprising a transition metal and as a ligand of 2,2'-bis[di-(3,5-dialkylphenyl)-phosphino]-1,1'-binaphthyl represented by formula (I):

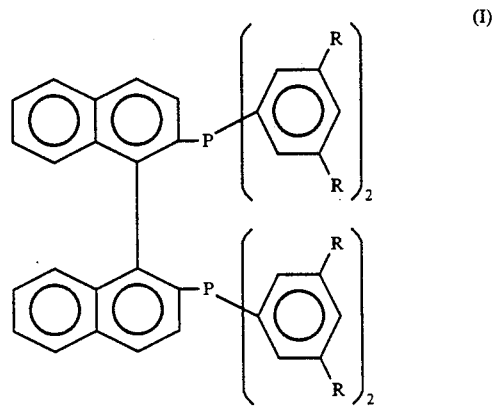

wherein R represents a lower alkyl group.

2. A transition metal catalyst as in claim 1, wherein said transition metal is rhodium, palladium, or ruthenium.

3. A transition metal catalyst as in claim 1, wherein R is an alkyl group having from 1 to 4 carbon atoms.

* * * * *